(12) United States Patent
Kim et al.

(10) Patent No.: US 8,241,679 B2
(45) Date of Patent: *Aug. 14, 2012

(54) COMPOSITION COMPRISING THE EXTRACT OF CRUDE DRUG COMPLEX HAVING NEUROPROTECTIVE ACTIVITY FOR PREVENTING AND TREATING STROKE AND NEURODEGENERATIVE DISEASES

(75) Inventors: Hocheol Kim, Seoul (KR); Young Min Boo, Seoul (KR)

(73) Assignee: Neumed Inc., Seoul (KR)

( * ) Notice: Subject to any disclaimer, the term of this patent is extended or adjusted under 35 U.S.C. 154(b) by 155 days.

This patent is subject to a terminal disclaimer.

(21) Appl. No.: 12/612,132

(22) Filed: Nov. 4, 2009

(65) Prior Publication Data

US 2010/0055213 A1   Mar. 4, 2010

Related U.S. Application Data

(63) Continuation-in-part of application No. 11/814,623, filed on Jul. 24, 2007, now Pat. No. 7,648,718.

(51) Int. Cl.
*A61K 36/258* (2006.01)
*A61K 36/539* (2006.01)
*A61K 36/00* (2006.01)

(52) U.S. Cl. ............ 424/728; 424/741; 424/725

(58) Field of Classification Search ............ None
See application file for complete search history.

(56) References Cited

U.S. PATENT DOCUMENTS

| 6,083,932 | A | 7/2000 | Pang et al. |
| 6,447,814 | B1 * | 9/2002 | Lee et al. .............. 424/725 |
| 2001/0026813 | A1 | 10/2001 | Kim et al. |

FOREIGN PATENT DOCUMENTS

| JP | 1994-316527 | 11/1994 |
| KR | 2002-0078850 | 10/2002 |
| KR | 2003-0049984 | 6/2003 |
| KR | 2004-0036451 | 4/2004 |
| KR | 2004-0079265 | 9/2004 |
| KR | 0458131 | 11/2004 |
| KR | 2005-0014710 | 2/2005 |
| WO | 00/61161 | 10/2000 |
| WO | 01/15717 | 3/2001 |
| WO | 03/006039 | 1/2003 |

OTHER PUBLICATIONS

Lee, et al., Protective effect of ginseng extract against apoptotic cell death induced by 2, 2', 5, 5'-tetrachlorobiphenyl in neuronal SK-N-MC cells, Life Sciences, 75(1313):1621-1634, 2004.

Van Kampen, et al., Neuroprotective actions of the ginseng extract G 115 in two rodent models of Parkinson's disease, Experimental Neurology, 184(11):521-529, 2003.
Lee, et al., Effects of ginsenoside Rd and decursinol on the neurotoxic responses induced by kainic acid in mice, Planta Med, 69(3):230-234, 2003.
Lee et al., Protective effect of ginsenosides, active ingredients of Panax ginseng, on kainic acid-induced neurotoxicity in rat hippocampus, Neuroscience Letters, 325:129-133, 2002.
Liao, et al., Neuroprotective effects of ginseng total saponin and ginsenosides Rb1 and Rg1 on spinal cord neurons in vitro, Experimental Neurology, 173:224-234, 2002.
Rudakewich, et al., Neurotrophic and neuroprotective actions of ginsenosides Rb(1) and Rg(1), Planta Med., 67:533-537, 2001.
Kim, et al., Dammarane derivatives protect cultured rat cortical cells from glutamate-induced neurotoxicity, Journal of Pharmacy and Pharmacology, 52(12):1505-1511, 2000.
Lim, et al., Protection of ischemic hippocampal neurons by ginsenoside Rb1, a main ingredient of ginseng root, Neuroscience Research, 28(3):191-200, 1997.
Wen, et al., Ginseng root prevents learning disability and neuronal loss in gerbils with 5-minute forebrain ischemia. Acta Neuropathol, 91:15-22, 1996.
Liu, et al., Protective effects of ginsenoside Rb1 and Rg1 on cultured hippocampal neurons, Yao Xue Xue Bao, 30:674-678, 1995.
Piao, et al., Neuroprotective effect of wogonin: Potential roles of inflammatory cytokines, Arch Pharm. Res., 27:930-936, 2004.
Cho, et al., Wogonin inhibits ischemic brain injury in a rat model of permanent middle cerebral artery occlusion, Biol. Pharm. Bull., 27:1561-1564, 2004.
Son, et al., Neuroprotective effect of wogonin in hippocampal slice culture exposed to oxygen and glucose deprivation, European Journal of Pharmacology, 493:99-102, 2004.
Lee, et al., Differential effects of natural polyphenols on neuronal survival in primary cultured central neurons against glutamate- and glucose deprivation-induced neuronal death, Brain Research, 986:103-113, 2003.
Kim, et al., Cytoprotective effect of *Scutellaria baicalensis* in CA1 hippocampal neurons of rats after global cerebral ischemia, Journal of Ethnopharmacology, 77(2):183-188, 2001.
Lee, et al., Flavonoid wogonin from medicinal herb is neuroprotective by inhibiting inflammatory activation of microglia, The FASEB Journal, 17:1943-1944, 2003.

* cited by examiner

*Primary Examiner* — Christopher R. Tate
*Assistant Examiner* — Deborah A. Davis
(74) *Attorney, Agent, or Firm* — Lucas & Mercanti, LLP

(57) ABSTRACT

The present invention relates to a composition comprising an extract of crude drug complex comprising *Panax ginseng* C. A. Meyer, *Acanthopanax senticosus* HARMS, *Angelica sinensis* DIELS, *Scutellaria baicalensis* GEORGI, prevention and treatment of stroke and neurodegenerative diseases such apoplexy, Alzheimer's disease (AD), Parkinson's disease (PD), Pick's disease, Creutzfeldt-Jakob disease and senile dementia.

11 Claims, 2 Drawing Sheets

[Fig. 1]
Control					Test
[Fig. 2]
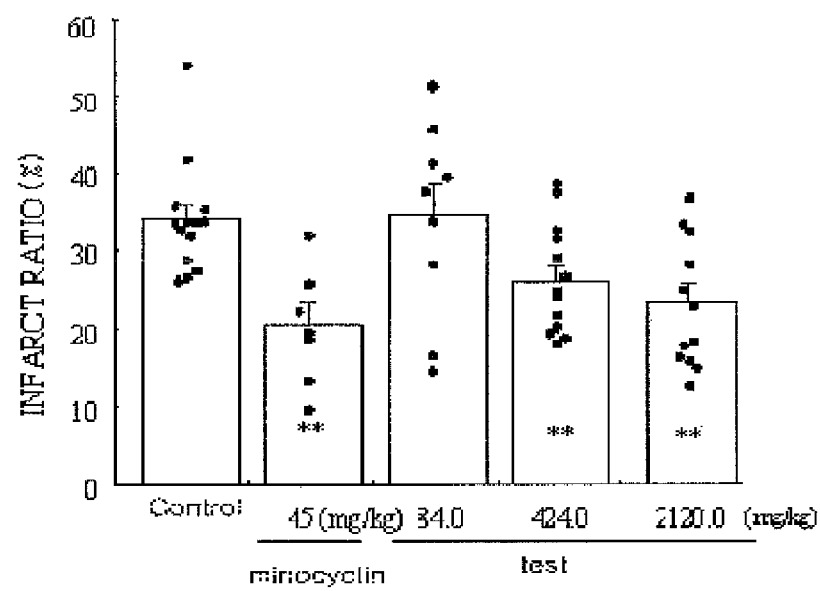
[Fig. 3]
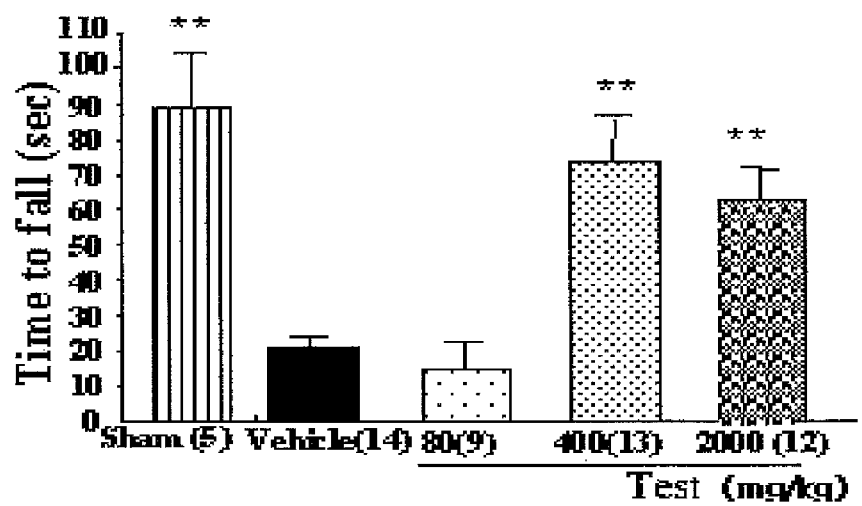

[Fig. 4]
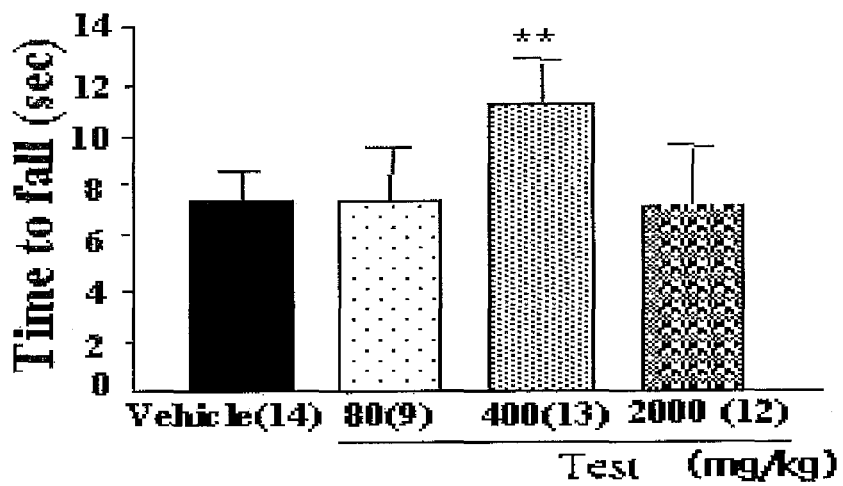
[Fig. 5]
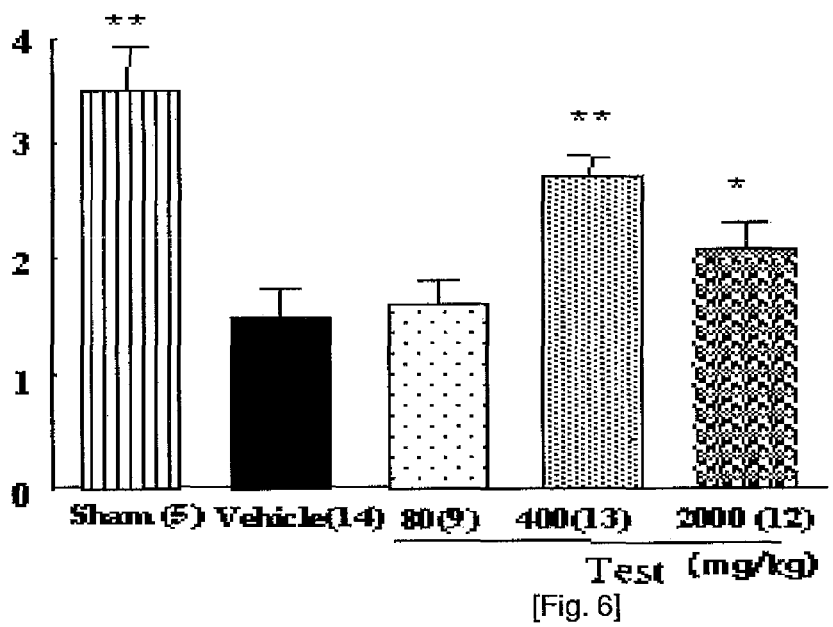
[Fig. 6]
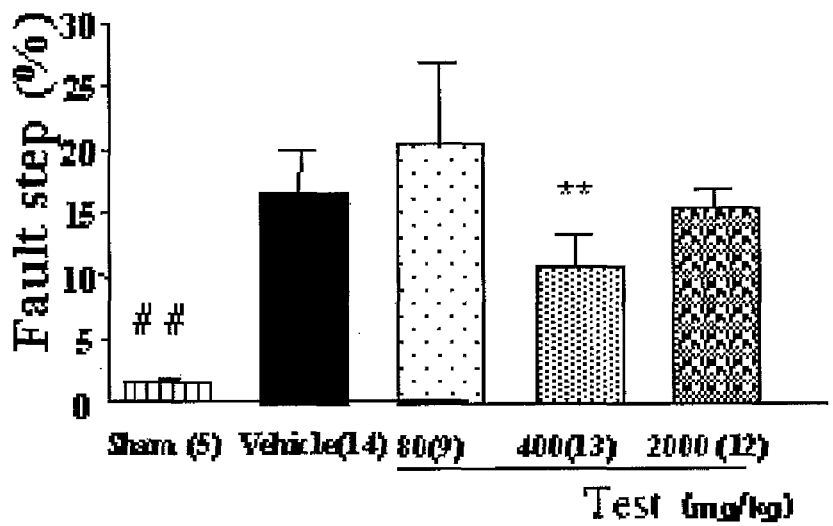

COMPOSITION COMPRISING THE EXTRACT OF CRUDE DRUG COMPLEX HAVING NEUROPROTECTIVE ACTIVITY FOR PREVENTING AND TREATING STROKE AND NEURODEGENERATIVE DISEASES

CROSS-REFERENCE TO RELATED APPLICATIONS

This application is a Continuation of U.S. application Ser. No. 11/814,623 filed Jul. 24, 2007, which is a 371 of PCT/KR2005/000199 filed on Jan. 25, 2005, the contents of each of which are incorporated herein by reference.

TECHNICAL FIELD

The present invention relates to an extract of crude drug complex having neuroprotective activity for preventing and treating stroke and neurodegenerative diseases.

BACKGROUND ART

In the twentieth century, as the average life span of human has been increasing with the rapid development of life science and medicine, new social problems including increased population ratio of older people are coming to the front, especially, the geriatric neuronal diseases such as stroke, Alzheimer's disease (AD), Parkinson's disease (PD) etc., which are fatal functional disorder of neuronal system, have been increased.

The growth, differentiation and death of neuronal cell in neuronal system are important control processes in general development the establishment of tissue specific function and the maintenance of homeostasis respectively.

Cerebrovascular disease is classified into two types, hemorrhagic brain disease and ischemic brain disease: the hemorrhagic brain disease such as cerebral hemorrhage occurs mainly by bleeding of cerebral vessels and the ischemic brain disease frequently occurring in older people is caused by the occlusion of cerebral vessels.

In case that temporary cerebral ischemia occurs, the supply of oxygen and glucose to brain is prevented and several syndrome such as ATP decrease and edema follows, which causes to exclusive range of brain injury as the result. After the considerable time lapses, the apoptosis of neuronal cell occurs, which is called as delayed neuronal death. The effect on the delayed type of neuronal death is performed by transient forebrain ischemic model using Mongolian gerbil and it has been reported that neuronal death occurs at CA1 region in hippocampus four days after the inducement of cerebral ischemia for 5 mins (Kirino T et al, *Acta Neuropathol.*, 62 pp 201-208, 1984; Kirino T, *Brain Res.*, 239, pp 57-69, 1982).

It has been reported that the neuronal death is caused by two mechanism; one is excitotoxic neuronal death mechanism; cerebral ischemia causes to excessive accumulation of outer glutamate and those glutamate are influxed into inner cell which causes to neuronal death by excessive accumulation of intracellular calcium ion (Kang T. C. et al, *J. Neurocytol.*, 30, pp 945-955, 2001) and another is oxidative neuronal death; the ischemia-reperfusion causing abrupt supply of oxygen results in the increase of free radical to give rise to the injury of DNA and cytoplasm (Won M. H. et al, *Brain Res.*, 836, pp 70-78, 1999; Sun A. Y. et al, *J. Biomed. Sci.*, 5, pp 401-141, 1998; Flowers F et al, *New Horiz*, 6, pp 169-180, 1998).

On the base of those mechanism study, there have been endeavored to develop effectively inhibiting substance of neuronal death or the mechanism thereof till now, however, neuroprotective agents have been nearly not yet found.

t-PA (tissue plasminogen activator), sole approved cerebral ischemia treating agent in FDA and sold in the market is a thrombolytic agent dissolving thrombus causing cerebral ischemia and inducing rapid supply of oxygen and glucose. Accordingly, it could not protect neuronal cell directly therefore it should be used urgently. Furthermore, since it is a thrombolytic agent, hemorrhagic cerebral disease occurs in case that it is administrated in over dose or too frequently.

MK-801, a potent NMDA receptor blocker effectively inhibiting initial calcium ion influx had been on clinical trial however it was abandoned because of its adverse action.

In Korea, lots of health care foods containing natural substance have been on the market however most of those are not yet authorized by scientific test and abused to give rise to scientific problems in the end.

Accordingly, it have been still needed to develop novel natural resource effective in treating and preventing cerebral disease through substantive and scientific experiments till now.

*Panax ginseng* C. A. Meyer belonged to Araliaceae, is distributed in Asian countries as well as other countries. It has been used as materials of Chinese medicine as a restorative and reported to comprise various ginseng saponins such as ginsenoside. Rb1, Rb2, Rc, Rd, Re, panaxadiol, panaxatriol, kaempferol etc (Chung B. S. and Shin M. K.; HyangyakDaesacheon, Youngrimsa, pp 439-444, 1998).

*Acanthopanax senticosus* HARMS belonged to Araliaceae, is distributed in humid area of Korea, Siberia etc. It has been used as materials of Chinese medicine as adatogenic activities, anti-inflammatory agents and reported to comprise various glycosides such as saponins, eleutherosides, essential oil etc (Chung B. S. and Shin M. K.; HyangyakDaesacheon, Youngrimsa, pp 433-435, 1998).

*Angelica sinensis* DIELS belonged to Umbelliferae, is distributed in China. It has been used as materials of Chinese medicine as a treating agent of various gynopathic diseases and reported to comprise various components such as ligustilide, butylidene phthalide, cnilide, isocnilide, nicotinic acid, sitosterol, essential oil etc (Chung B. S. and Shin M. K.; HyangyakDaesacheon, Youngrimsa, pp 406-408, 1998).

*Scutellaria baicalensis* GEORGI belonged to Labiatae, is distributed in Korea, China, Siberia etc. It has been used as materials of Chinese medicine as a diuretics, anti-inflammatory agent, cholagogue, etc and reported to comprise various components such as baicalin, baicalin, woginin, wogonoside, scutellarein, hispidulin etc (Chung B. S. and Shin M. K.; HyangyakDaesacheon, Youngrimsa, pp 864-865, 1998).

However, there has been not reported or disclosed about therapeutic effect for brain disease of the crude drug complex comprising *Panax ginseng* C. A. Meyer, *Acanthopanax senticosus* HARMS, *Angelica sinensis* DIELS, *Scutellaria baicalensis* GEORGI, in any of above cited literatures, the disclosures of which are incorporated herein by reference.

To investigate an effect of the extract of above described crude drug complex on the neuronal growth and differentiation through several biochemical experiments and to confirm whether the extract play an important role in inhibiting neuronal apoptosis, main cause of stroke and neurodegenerative diseases, the inventors of the present invention have intensively carried out 4 sensory motor function tests using animal model, and finally completed present invention by confirming that the extract inhibit the neuronal apoptosis, and show neuroprotective activity.

These and other objects of the present invention will become apparent from the detailed disclosure of the present invention provided hereinafter.

DISCLOSURE OF INVENTION

Technical Problem

In case that temporary cerebral ischemia occurs, the supply of oxygen and glucose to brain is prevented and several syndrome such as ATP decrease and edema follows, which causes to exclusive range of brain injury as the result. After the considerable time lapses, the apoptosis of neuronal cell occurs, which is called as delayed neuronal death. The effect on the delayed type of neuronal death is performed by transient forebrain ischemic model using Mongolian gerbil and it has been reported that neuronal death occurs at CA1 region in hippocampus four days after the inducement of cerebral ischemia for 5 mins (Kirino T et al, *Acta Neuropathol.*, 62 pp 201-208, 1984; Kirino T, *Brain Res.*, 239, pp 57-69, 1982).

It has been reported that the neuronal death is caused by two mechanism; one is excitotoxic neuronal death mechanism; cerebral ischemia causes to excessive accumulation of outer glutamate and those glutamate are influxed into inner cell which causes to neuronal death by excessive accumulation of intracellular calcium ion (Kang T. C. et al, *J. Neurocytol.*, 30, pp 945-955, 2001) and another is oxidative neuronal death; the ischemia-reperfusion causing abrupt supply of oxygen results in the increase of free radical to give rise to the injury of DNA and cytoplasm (Won M. H. et al, *Brain Res.*, 836, pp 70-78, 1999; Sun A. Y. et al, *J. Biomed. Sci.* 5, pp 401-141, 1998; Flowers F et al, *New Horiz*, 6, pp 169-180, 1998).

On the base of those mechanism study, there have been endeavored to develop effectively inhibiting substance of neuronal death or the mechanism thereof till now, however, neuroprotective agents have been nearly not yet found.

t-PA (tissue plasminogen activator), sole approved cerebral ischemia treating agent in FDA and sold in the market is a thrombolytic agent dissolving thrombus causing cerebral ischemia and inducing rapid supply of oxygen and glucose. Accordingly, it could not protect neuronal cell directly therefore it should be used urgently. Furthermore, since it is a thrombolytic agent, hemorrhagic cerebral disease occurs in case that it is administrated in over dose or too frequently.

MK-801, a potent NMDA receptor blocker effectively inhibiting initial calcium ion influx had been on clinical trial however it was abandoned because of its adverse action.

In Korea, lots of health care foods containing natural substance have been on the market however most of those are not yet authorized by scientific test and abused to give rise to scientific problems in the end.

Technical Solution

Accordingly, it is an object of the present invention to provide a pharmaceutical composition comprising an extract of crude drug complex comprising *Panax ginseng* C. A. Meyer, *Acanthopanax senticosus* HARMS, *Angelica sinensis* DIELS, *Scutellaria baicalensis* GEORGI as an active ingredients for the treatment and prevention of stroke and neurodegenerative diseases by protecting neuronal cell.

Preferably, above described extract of crude drug complex comprising *Panax ginseng* C. A. Meyer, *Acanthopanax senticosus* HARMS, *Angelica sinensis* DIELS, *Scutellaria baicalensis* GEORGI is mixed in the ratio of 1-5:2-7:2-7:1, more preferably, 2:5:4:1.

Above described extract comprises the extract prepared by extracting plant material with water, lower alcohols such as methanol ethanol, preferably methanol, or the mixtures thereof.

It is an object of the present invention to provide a use of an extract of crude drug complex comprising *Panax ginseng* C. A. Meyer, *Acanthopanax senticosus* HARMS, *Angelica sinensis* DIELS, *Scutellaria baicalensis* GEORGI for the preparation of therapeutic agent for the treatment and prevention of stroke and neurodegenerative diseases by protecting neuronal cell in human or mammal in need thereof.

It is an object of the present invention to provide a method of treating or preventing stroke and neurodegenerative diseases by protecting neuronal cell in a mammal comprising administering to said mammal an effective amount of an extract of crude drug complex comprising *Panax ginseng* C. A. Meyer, *Acanthopanax senticosus* HARMS, *Angelica sinensis* DIELS, *Scutellaria baicalensis* GEORGI, together with a pharmaceutically acceptable carrier thereof.

It is another object of the present invention to provide a health food or food additives comprising an extract of crude drug complex comprising *Panax ginseng* C. A. Meyer, *Acanthopanax senticosus* HARMS, *Angelica sinensis* DIELS, *Scutellaria baicalensis* GEORGI, together with a sitologically acceptable additive for the prevention and improvement of stroke and neurodegenerative diseases by protecting neuronal cell.

Above described neurodegenerative diseases comprises apoplexy, Alzheimer's disease (AD), Parkinson's disease (PD), Pick's disease, Creutzfeldt-Jakob disease, senile dementia and the like.

The pharmaceutical composition of the present invention can contain about 0.01~50% by weight of the above extract based on the total weight of the composition.

The health food of the present invention comprises above extracts as 0.01 to 80%, preferably 1 to 50% by weight based on the total weight of the composition.

Above health food can be contained in health food, health beverage etc, and may be used as powder, granule, tablet, chewing tablet, capsule, beverage etc.

An inventive extract may be prepared in accordance with the following preferred embodiment.

Hereinafter, the present invention is described in detail.

An inventive extract of the present invention can be prepared in detail by following procedures, The inventive crude extract of crude drug complex comprising *Panax ginseng* C. A. Meyer, *Acanthopanax senticosus* HARMS, *Angelica sinensis* DIELS, *Scutellaria baicalensis* GEORGI, can be prepared by follows; all the dried materials excepting *Scutellaria baicalensis* GEORGI is dried, cut, crushed and mixed with 5 to 25-fold, preferably, approximately 10 fold volume of distilled water, lower alcohols such as methanol, ethanol, butanol and the like, or the mixtures thereof, preferably hot water; the solution is treated with hot water at the temperature ranging from 20 to 100° C., preferably from 60 to 100° C., for the period ranging from 1 to 24 hrs with extraction method by the extraction with hot water, cold water, reflux extraction, or ultrasonication extraction with 1 to 5 times, preferably 2 to 3 times, consecutively; the residue is added to honey and remaining dried *Scutellaria baicalensis* GEORGI to be subjected to further extraction with hot water for the period ranging from 48 to 120 hrs, preferably, 96 hrs; and the collected extract is filtered to obtain the supernatant to be concentrated with rotary evaporator at the temperature ranging from 20 to 100° C., preferably from 50 to 70° C. and then dried by vacuum freeze-drying, hot air-drying or spray drying to obtain dried extract powder of the crude drug complex which can be soluble in water, lower alcohol, or the mixtures thereof.

In an alternative embodiment of the present invention, the extract of crude drug of the present invention can be prepared by the procedure comprising the steps consisting of; (a), adding dried *Panax ginseng* C. A. Meyer and *Acanthopanax senticosus* HARMS to 5 to 25-fold, preferably, 2 to 8-fold volume of distilled water, lower alcohols such as methanol, ethanol, butanol and the like, or the mixtures thereof preferably hot water and extracting at the temperature ranging from 20 to 100° C., preferably from 60 to 100° C., for the period ranging from 1 to 24 hrs with reflux extraction to collect their extract, filtering and drying to obtain concentrated extract; (b) adding the mixture consisting of the extract of *Poria cocos* WOLF and *Rehmania gluticosa* L, and honey thereto and extracting with hot water for the period ranging from 48 to 120 hrs, preferably 96 hrs with the addition of the extract of *Scutellaria baicalensis* GEORGI to obtain crude complex drug extract of the present invention.

Accordingly, present invention also provides the extract of crude drug complex prepared by above described preparation method.

Additionally, polar solvent soluble and non-polar solvent soluble extract of present invention can be prepared by following procedure; the crude extract prepared by above step is suspended in water, and then is mixed with 1 to 100-fold, preferably, 1 to 5-fold volume of non polar solvent such as ethyl acetate, chloroform, hexane and the like; the non-polar solvent soluble layer is collected to obtain non-polar solvent soluble extract of the present invention and remaining polar solvent soluble layer is collected to obtain polar solvent soluble extract of the present invention which is soluble in water, lower alcohol, or the mixture thereof. Also, above described procedures may be modified or subjected to further step to fractionate or isolate more potent fractions or compounds by conventional procedure well-known in the art, for example, the procedure disclosed in the literature (Harborne J. B. Phytochemical methods: *A guide to modern techniques of plant analysis*, $3^{rd}$ Ed. pp 6-7, 1998).

Through the experiment to investigate the effect of the extract of above described crude drug complex on neuronal injury caused by regional cerebral ischemia occurred in MCAo animal model, it is confirmed that the extract inhibits the neuronal apoptosis caused by regional cerebral ischemia and shows neuroprotective activity.

In accordance with another aspect of the present invention, there is provided a pharmaceutical composition comprising the extract of above described crude drug complex prepared by above described preparation method for the treatment and prevention of stroke and neurodegenerative diseases by protecting neuronal cell as active ingredients.

It is another of the present invention to provide method of treating or preventing stroke and neurodegenerative diseases by protecting neuronal cell in a mammal comprising administering to said mammal an effective amount of an extract of above described crude drug complex prepared by above preparation method.

The inventive composition for treating and preventing stroke and neurodegenerative diseases by protecting neuronal cell, may comprises above extracts as 0.01~50% by weight based on the total weight of the composition.

The inventive composition may additionally comprise conventional carrier, adjuvants or diluents in accordance with a using method well known in the art. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, antiagglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 10 g/kg, preferably, 1 to 3 g/kg by weight/day of the inventive extract of the present invention. The dose may be administered in single or divided into several times per day. In terms of composition, the amount of inventive extract should be present between 0.01 to 50% by weight, preferably 0.5 to 40% by weight based on the total weight of the composition.

The pharmaceutical composition of present invention can be administered to a subject animal such as mammals (rat, mouse, domestic animals or human) via various routes. All routes of administration are contemplated, for example, administration can be made orally, rectally or by intravenous, intramuscular, subcutaneous, intracutaneous, intrathecal, epidural or intracerebroventricular injection.

Also, the present invention provide a health food comprising an extract of crude drug complex consisting of *Panax ginseng* C. A. Meyer, *Acanthopanax senticosus* HARMS, *Angelica sinensis* DIELS, *Scutellaria baicalensis* GEORGI, together with a sitologically acceptable additive for the prevention and improvement of stroke and neurodegenerative diseases by protecting neuronal cell. The health food can be prepared by adding 0.01 to 80 w % of above described extracts, amino acids 0.001 to 5% by weight, vitamins 0.001 to 2% by weight, sugars 0.001 to 20% by weight, organic acids 0.001 to 10% by weight and proper amount of sweetener and flavors sitologically acceptable food additive.

Above described extract of above described crude drug complex can be added to food and beverage for the prevention and improvement of stroke and neurodegenerative diseases by protecting neuronal cell.

To develop for health food, examples of addable food comprising above extracts of the present invention are various food, beverage, gum, vitamin complex, health improving food and the like, and can be used as power, granule, tablet, chewing tablet, capsule or beverage etc.

Also, the extract of the present invention could prevent and improve stroke and neurodegenerative diseases by protecting neuronal cell by comprising to child and infant food, such as modified milk powder, modified milk powder for growth period, modified food for growth period.

Above described composition therein can be added to food, additive or beverage, wherein, the amount of above described extract in food or beverage may generally range from about 0.1 to 80 w/w %, preferably 1 to 50 w/w % of total weight of food for the health food composition and 1 to 30 g, preferably 3 to 10 g on the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cy- clodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartame et al., may be useful favorably. The amount of above described natural carbohydrate is generally ranges from about 1 to 20 g, preferably 5 to 12 g in the ratio of 100 ml, of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The inventive composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, α-tocopherol, rosemary extract, vitamin C, green tea extract, licorice root extract, chitosan, tannic acid, phytic acid etc.

The above-described extract of the present invention may be 20 to 90% high concentrated liquid, power, or granule type.

Similarly, the above described extract of the present invention can additionally comprise at least one lactose, casein, dextrose, glucose, sucrose and sorbitol.

Inventive extract of the present invention have no toxicity and adverse effect therefore; they can be used with safe.

It will be apparent to those skilled in the art that various modifications and variations can be made in the compositions, use and preparations of the present invention without departing from the spirit or scope of the invention.

BRIEF DESCRIPTION OF THE DRAWINGS

The above and other objects, features and other advantages of the present invention will more clearly understood from the following detailed description taken in conjunction with the accompanying drawings, in which;

FIG. 1 shows a photograph of brain sections stained with TIC and photographed by digital camera after 2 hrs of MCAo and 24 hrs of reperfusion showing infarction (white area indicates infarct area and red area indicates intact area);

FIG. 2 shows a comparison figure showing the neuroprotective effects of control, positive control and inventive extract on MCAo in rats, each black dot represents individual value for each rat;

FIG. 3 to 6 shows the recovery effect of inventive extract on the sensory locomotive function, FIG. 3 shows the result of rotarod test determined at 20 hrs, FIG. 4 prehensile traction test determined at 21 hrs, FIG. 5 beam balance test determined at 22 hrs, FIG. 6 foot fault test determined at 23 hrs after MCAo.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

The following Reference Example, Examples and Experimental Examples are intended to further illustrate the present invention without limiting its scope.

EXAMPLE 1

Preparation of the Extract of Crude Drug Complex (1)

660 g of dried *Panax ginseng* C. A. Meyer was cut into small pieces, mixed with 3 L of distilled water and the mixture was subjected to reflux extraction for 2 hrs. The extract was concentrated under reduced pressure and dried with freezing dryer (Speed Spec 3000, Bio-Rad Co. U.S.A.) to obtain 200 g of dried crude extract. The similar procedure to above described method was performed for 300 g of *Acanthopanax senticosus* HARMS to obtain 20 g of the dried extract, 350 g of *Angelica sinensis* DIELS to obtain 50 g of the dried extract, 80 g of *Scutellaria baicalensis* GEORGI to obtain 10 g of the dried extract, respectively.

The extract of four crude drugs prepared in above described step was mixed in the mix ratio of 2:5:4:1 based on the weight of dried crude drug and used as test samples in following experiments.

EXAMPLE 2

Preparation of the Extract of Crude Drug Complex (2)

1,200 g of dried four crude drug mixture, i.e., *Panax ginseng* C. A. Meyer, *Acanthopanax senticosus* HARMS, *Angelica sinensis* DIELS and *Scutellaria baicalensis* GEORGI mixed with the ratio of 2:5:4:1 was added to 3 L of distilled water and the mixture was subjected to reflux extraction for 2 hrs. The extract was concentrated under reduced pressure and dried with freezing dryer (Speed Spec 3000, Bio-Rad Co. U.S.A.) to obtain 163.54 g of dried crude extract.

The extract of four crude drugs prepared in above described step was used as test samples in following experiments.

EXPERIMENTAL EXAMPLE 1

MCAo Experimental Model

To determine the preventing effect of the extract of crude drug complex of the present invention on neuronal injury, following intraluminal suture method using animal model was performed by modifying well-mown method disclosed in the literature (Zea L. E. *Stroke*, 20, pp 84-91, 1989).

The procedure and experimental method used in Experimental Examples was described as follows:

Method 8-weeks old white male Sprague-Dawley rat weighing about 280 g was procured from Samtaco Co. Ltd. (Seoul), fasted up for 1 week providing with free access to water and feed and acclimated to experimental environment.

The rat was anesthetized with 5% isoflurane gas (mixed gas with the gas mixture consisting of 70% $N_2O$ and 30% $O_2$ gas and 5% isoflurane) and maintained with 1% isoflurane gas during experiment.

The skin at the center of rat neck was excised and right CCA (common carotid artery) and ECA (external carotid artery) were isolated from neighboring tissue and nerves with care. CCA and ECA were ligated with ligature and ICA (Internal Carotid Artery) and pterygopalatine artery were also isolated and ligated in similar manner to above procedure. ICA near by bifurcation was partially excised with scissors and the blood vessel was pored to insert probe. The probe was made by the step consisting that 23 mm of 4-0 nylon thread was coated with silicone component such as Polysiloxan solidified with activator to increase their adhesive force to blood vessel. ICA was ligated at the point that about 10 mm of coated probe was inserted to reach at 20 mm or the less from the inserting point and the resistance was felt. The probe was fixed at the same time preventing regurgitation. The skin excision area was sealed again and the rat was restored from anesthetized status naturally. inserted probe obstruct the blood flow of MCA, the regional ischemia was induced. After 2 hrs, the rat was re-anesthetized to remove the probe restoring carotid blood flow. And then, after 22 hrs, the rat was sacrificed by cervical dislocation to deliver brain and the brain tissue was examined by microscope.

The body temperature was monitored and maintained at 37±0.5° C.

The caudal was excised and terminal tissue was discarded to obtain 6 numbers of brain slices with the thickness of 2 mm using by brain matrix. Optimum amount of 2% triphenyltetrazolium chloride (2,3,5-triphenyltetrazolium-chloride: TTC) solution diluted with saline solution, was poured into 9 well plates. The brain slices were added thereto and stained at 37° C. for 30 rains. The stained tissues were photographed by digital camera (Olympus Co. c2500L model, USA) and the images were transferred to computer. The volume of cerebral infarction region was calculated by the OPTIMAS program (Media Cybernetics Co., 6.51 version). To determine the exact volume of cerebral infarction region of right hemisphere excluding edema volume (A), the real volume of cerebral infarction (B) was calculated by following Empirical Formula 1 and 2.

The volume of infarcted hemisphere tissue induced cerebral ischemia ($mm^3$)=(The volume of left hemisphere to which ischemia was not induced)–(The volume of right hemisphere which ischemia was induced but has no tissue infarction) [Empirical Formula 1]

The volume percentage of total infarcted hemisphere tissue induced cerebral ischemia (%)=(The volume of infarcted hemisphere tissue induced cerebral ischemia)÷(The volume of left hemisphere to which ischemia was not induced)×100 [Empirical Formula 2]

Drug Treatment

Animals in the control group were administrated with distilled water (3 mg/kg, po) at 0 and 2 hrs after the occlusion. In sample treatment groups were orally administrated with the same volume of the extract prepared in Examples with various concentrations i.e., 80, 400 and 2000 mg/kg twice at 0 and 2 hrs after the occlusion respectively. To avoid of dilatation of brain artery during MCAo and to confirm the neuroprotective effect of the drugs, we administrated twice at 2 hrs and 4 hrs after the occlusion. For the positive control group, animals were treated with 45 mg/kg of minocycline in the same way.

FIGS. 1 and 2 show the determined result of the experiment confirming the effect of the extract on the neuronal injury. As can be seen in FIG. 1, test group treated with the extract of crude drug complex shows smaller darkish red area stained with TTC compared with control group, which means that the test groups have potent preventing effect on the neuronal injury. White area indicates infarct area and red area indicated the intact area.

As can be seen in FIG. 2, the infarct volume of control group and test group are 33.3±1.17% and 34.7±1.77% whereas the positive control group treated with 45 mg/kg of minocycline is 20.5±2.85%. The volume percentage of total infarcted hemisphere tissue induced cerebral ischemia (%) treated with various concentrations of the inventive extract i.e., 80, 400 and 2000 mg/kg at 0 and 120 mins after MCAo showed reduced infarct volume to 34.7±4.19, 25.6±1.86, and 23.4±2.40% respectively. Accordingly, it is confirmed that the extract of crude drug complex shows preventing activity of cerebral ischemia in dose dependent manner. Especially, the test groups treated with 400 and 2000 mg/kg protect cerebral ischemia by 29 and 34% respectively, which showed about 70% and 81% of neuroprotective effect compared with that of positive control.

EXPERIMENTAL EXAMPLE 2

The Recovery Effect on the Sensory Motor Function in MCAo Rat Model

To determine the preventing effect of the extract of crude drug complex of the present invention on the improvement effect of the sensory motor function, following behavior tests using animal model, i.e., rotarod test, prehensile traction test, balance beam test and foot fault test was performed by modifying well-known method disclosed in the literatures.

2-1. Rotarod Test

Rotarod test is one of most correlated test with cerebral injury such as stroke or spinal cord neuronal model and appropriate to evaluating the sensory motor function. Rotarod test was performed at 20 hrs after ischemia. This test measures animal's ability to balance and coordinate the components of general motor function. Rota-rod (Ugo basile, Italy) was accelerated rotation from 0 rpm to 25 rpm within 2 min. The latency time was determined in five separate trials for each rat and excluded lowest and highest data.

As can be seen in FIG. 3, the test group treated with inventive extract showed significant improvement in balance and coordination components of general motor function compared with that of control group. While sham operated group showed 92.4±15.92 sec ($p<0.01$), control group showed 24.8±6.32 sec, the test groups treated with 80, 400 and 2000 mg/kg of inventive extract showed 15±7.14, 74.1±12.59 ($p<0.01$) and 63.1±10.08 sec ($p<0.01$) respectively.

In test group treated with 400 mg/kg of inventive extract showed the maximum effects on this test.

2-2. Prehensile Traction Test

Prehensile traction test was performed by the modified method described in previous literature (Wallace et al., *J. Gerontol.*, 35, pp 364-370, 1980). This test was done at 21 hrs after ischemia. This test is appropriate to measure the muscle strength. A rat was suspended from the square wooden rod (3 cm wide, 1.5 m long) at 40 cm height above the surface until it grasped it with 4 paws. Then the rat was released and the time fell off was measured. A pad of rubber cushion (about 3 cm thick) was placed beneath the rod to cushion the rats fall.

As can be seen in FIG. 4, the test group treated with inventive extract showed significant improvement in muscle strength with that of control group. control group showed 6.6±0.90 sec, the test groups treated with 80, 400 and 2000 mg/kg of inventive extract showed 7.2±2.08, 11.0±1.58 ($p<0.05$) and 7.0±2.31 see, respectively. In test group treated with 400 mg/kg of inventive extract showed the maximum effects on this test after MCAo.

2-3. Balance Beam Test

Balance beam was performed by the modified method described in previous literature (Puurunen et al., *Neuropharmacology*, 40, pp 597-606, 2001). This test is appropriate to assess deficits of the vestibulomotor function. The balance beam was a square beam (2.5 cm wide, 122 cm long, at a height of 42 cm). After laying the rat on middle of the beam crossly, the score was rated as follows: the rat was not able to stay on the beam, 0 points; the rat did not move, but was able to stay on the beam, 1 point; the rat tried to turn left or right side of the beam, 2 points; the rat turned left or right side and walk on the beam with more than 50% foot slips of the affected hind limb, 3 points; the rat traversed the beam with more than one foot slip, but less than 50%, 4 points; the rat had only one slip of the hind limb, 5 points; the rat traversed the beam without any slips of the hind limb, 6 points.

As can be seen in FIG. 5, the test group treated with inventive extract showed significant improvement in motor coordination and integration of motor movement with that of control group. While sham operated group showed 3.4±0.39 points ($p<0.01$), control group showed 1.5±0.19 points, the test groups treated with 80, 400 and 2000 mg/kg of inventive extract showed 1.6±0.25, 2.7±0.18 ($p<0.01$) and 2.1±0.23 points ($p<0.05$) respectively. In 400 mg/kg treated group also showed the maximum effects on this test after MCAo. In test group treated with 400 mg/kg of inventive extract showed the maximum effects on this test after MCAo.

2-4. Foot Fault Test

Foot fault test was performed by the modified method described in previous literature (Markgraf C. G., et al; *Brain Res.*, 575, pp 238-246, 1992). This test is appropriate to measure animals' ability to integrate motor responses during locomotion. Rats were placed on an elevated grid surface (23.5 cm wide, 43.5 cm long, 92 cm high; 2.5 cm square/grid opening, 2 mm diameter grid wire). Fault steps were counted when a foot was misplaced and fall through a grid opening. We counted for 60 see right foot fault and total number of forelimb's steps as the percentage of right limb foot fault.

As can be seen in FIG. 6, the test group treated with inventive extract showed significant improvement in sensorimotor integration and forelimb responses to visual, tactile and proprioceptive stimuli with that of control group. While sham operated group showed 1.6±0.14% ($p<0.01$), control group showed 16.6±2.87%, the test groups treated with 80, 400 and 2000 mg/kg of inventive extract showed 20.5±6.25, 10.7±2.25 ($p<0.01$) and 15.4±2.12% respectively. In test group treated with 400 mg/kg of inventive extract showed the maximum effects on this test after MCAo.

EXPERIMENTAL EXAMPLE 3

Toxicity Test

Methods (1)

The acute toxicity tests on ICR mice (mean body weight 25+5 g) and Sprague-Dawley rats (235±10 g, Jung-Ang Lab Animal Inc.) were performed using the extract prepared in the Example 1. Four group consisting of 10 mice or rats was administrated orally intraperitoneally with 250 mg/kg, 500 mg/kg, 1000 mg/kg and 5000 mg/kg of test sample or solvents (0.2 ml, i.p.) respectively and observed for 2 weeks.

Methods (2)

The acute toxicity tests on ICR mice and Sprague-Dawley rats were performed using the extract prepared in the Example 1. Four group consisting of 10 mice or rats was administrated intraperitoneally with 25 mg/kg, 250 mg/kg, 500 mg/kg and 725 mg/kg of test sample or solvents (0.2 ml, i.p.), respectively and observed for 24 hrs.

Results

There were no treatment-related effects on mortality, clinical signs, body weight changes and gross findings in any group or either gender. These results suggested that the extract of the present invention were potent and safe.

Hereinafter, the formulating methods and kinds of excipients will be described, but the present invention is not limited to them. The representative preparation examples were described as follows.

Preparation of Powder

Dried powder of Example 1-1 . . . 50 mg

Lactose . . . 100 mg

Talc . . . 10 mg

Powder preparation was prepared by mixing above components and filling sealed package.

Preparation of Tablet

Dried powder of Example 1-1 . . . 50 mg

Corn Starch . . . 100 mg

Lactose . . . 100 mg

Magnesium Stearate . . . 2 mg

Tablet preparation was prepared by mixing above components and entabletting.

Preparation of Capsule

Dried powder of Example 1-1 . . . 50 mg

Corn starch . . . 100 mg
Lactose . . . 100 mg
Magnesium Stearate . . . 2 mg

Tablet preparation was prepared by mixing above components and filling gelatin capsule by conventional gelatin preparation method.

Preparation of Injection
Dried powder of Example 1-1 . . . 50 mg
Distilled water for injection . . . optimum amount
PH controller . . . optimum amount Injection preparation was prepared by dissolving active component, controlling pH to about 7.5 and then filling all the components in 2 ml ample and sterilizing by conventional injection preparation method.

Preparation of Liquid
Dried powder of Example 1-2 . . . 0.1~80 g
Sugar . . . 5~10 g
Citric acid . . . 0.05~0.3%
Caramel . . . 0.005~0.02%
Vitamin C . . . 0.1~1%
Distilled water . . . 79~94%
$CO_2$ gas . . . 0.5~0.82%

Liquid preparation was prepared by dissolving active component, filling all the components and sterilizing by conventional liquid preparation method.

Preparation of Health Food
Extract of Example 1-2 . . . 1000 mg
Vitamin mixture . . . optimum amount
Vitamin A acetate . . . 70 mg
Vitamin E . . . 1.0 mg
Vitamin $B_1$ . . . 0.13 mg
Vitamin $B_2$ . . . 0.15 mg
Vitamin B6 . . . 0.5 mg
Vitamin B12 . . . 0.2 mg
Vitamin C . . . 10 mg
Biotin . . . 10 mg
Amide nicotinic acid . . . 1.7 mg
Folic acid . . . 50 mg
Calcium pantothenic acid . . . 0.5 mg
Mineral mixture . . . optimum amount
Ferrous sulfate . . . 1.75 mg
Zinc oxide . . . 0.82 mg
Magnesium carbonate . . . 25.3 mg
Monopotassium phosphate . . . 15 mg
Dicalcium phosphate . . . 55 mg
Potassium citrate . . . 90 mg
Calcium carbonate . . . 100 mg
Magnesium chloride . . . 24.8 mg The above-mentioned vitamin and mineral mixture may be varied in many ways. Such variations are not to be regarded as a departure from the spirit and scope of the present invention.

Preparation of Health Beverage
Extract of Example 1 . . . 1000 mg
Citric acid . . . 1000 mg
Oligosaccharide . . . 100 g
Apricot concentration . . . 2 g
Taurine . . . 1 g
Distilled water . . . 900☐

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Industrial Applicability

As described in the present invention, the extract of *Panax ginseng* C. A. Meyer, *Acanthopanax senticosus* HARMS, *Angelica sinensis* DIELS and *Scutellaria baicalensis* GEORGI, has potent neuroprotective activity occurred in cerebral ischemia, therefore, it can be used as the therapeutics or health food for treating and preventing stroke and neurodegenerative diseases.

The invention claimed is:

1. A pharmaceutical composition comprising an effective amount of extract of crude drug complex, wherein the crude drug complex comprises *Panax ginseng* C. A. Meyer, *Acanthopanax senticosus* HARMS, *Angelica sinensis* DIELS and *Scutellaria baicalcnsis* GEORGI as active ingredients for improving recovery of sensory motor function damaged by cerebral ischemia.

2. The pharmaceutical composition according to claim 1, wherein said crude drug complex is extracted with a solvent selected from the group consisting of water, lower alcohol and the mixture thereof.

3. A health food comprising an effective amount of extract of crude drug complex, wherein the crude drug complex consists of *Panax ginseng* C. A. Meyer, *Acanthopanax senticosus* HARMS, *Angelica sinensis* DIELS, *Scutellaria baicalensis* GEORGI as active ingredients, for improving recovery of sensory motor function damaged by cerebral ischemia.

4. The health food according to claim 3, wherein said crude drug complex is extracted with a solvent selected from the group consisting of water, lower alcohol and the mixture thereof.

5. The health food according to claim 3, wherein said health food further comprises one selected from the group consisting of amino acids, vitamins, sugars, organic acids, sweeteners and combination thereof.

6. The health food according to claim 3, wherein said health food is provided as powder, granule, tablet, chewing tablet, capsule or beverage type.

7. A method for improving recovery of sensory motor function damaged by cerebral ischemia by protecting neuronal cell comprising:
administering to a subject in need thereof with a composition comprising an effective amount of extract of crude drug complex, wherein the crude drug complex comprises *Panax ginseng* C. A. Meyer, *Acanthopanax senticosus* HARMS, *Angelica sinensis* DIELS and *Scuteliaria baicalensis* GEORGI as active ingredients.

8. The method according to claim 7, wherein said crude drug complex is extracted with a solvent selected from the group consisting of water, lower alcohol and the mixture thereof.

9. The method according to claim 7, wherein said composition is a health food.

10. The method according to claim 9, wherein said health food further comprises one selected from the group consisting of amino acids, vitamins, sugars, organic acids, sweeteners and combination thereof.

11. The method according to claim 9, wherein said health food is provided as powder, granule, tablet, chewing tablet, capsule or beverage type.

* * * * *